(12) United States Patent
Wang

(10) Patent No.: US 9,678,051 B2
(45) Date of Patent: Jun. 13, 2017

(54) METHOD FOR DISTINGUISHING, CLASSIFYING AND MEASURING SOFT AND HARD INCLUSIONS IN LIQUID METAL

(75) Inventor: Xiaodong Wang, Ilmenau (DE)

(73) Assignee: UNIVERSITY OF CHINESE ACADEMY OF SCIENCES, Beijing (CN)

( * ) Notice: Subject to any disclaimer, the term of this patent is extended or adjusted under 35 U.S.C. 154(b) by 662 days.

(21) Appl. No.: 13/046,434

(22) Filed: Mar. 11, 2011

(65) Prior Publication Data

US 2012/0229154 A1    Sep. 13, 2012

(51) Int. Cl.
*G01R 27/08*    (2006.01)
*G01N 33/20*    (2006.01)
*G01N 27/07*    (2006.01)

(52) U.S. Cl.
CPC ........... *G01N 33/206* (2013.01); *G01N 27/07* (2013.01)

(58) Field of Classification Search
CPC ...................... G01N 33/206; G01N 27/07
USPC .......................................... 324/693; 148/509
See application file for complete search history.

(56) References Cited

U.S. PATENT DOCUMENTS

| | | | |
|---|---|---|---|
| 7,084,646 B2* | 8/2006 | Gruebler et al. | 324/693 |
| 2001/0035747 A1* | 11/2001 | Li et al. | 324/71.4 |
| 2004/0201371 A1* | 10/2004 | Conti | 324/71.1 |

* cited by examiner

*Primary Examiner* — Daniel Miller
(74) *Attorney, Agent, or Firm* — Gokalp Bayramoglu

(57) ABSTRACT

The present invention is a method for distinguishing, classifying and measuring soft and hard inclusions in a liquid metal that includes obtaining a flow through cell disposed on a tube with a top to allow the liquid metal to flow through the flow through cell and into the tube. There is also a mounting and a vacuum system disposed on top of the tube to draw the liquid metal through the flow through cell and into the tube that utilizes a pair of electrodes set inside and outside of the tube to apply an electric current to the liquid metal passing through the flow through cell. An electric resistance change is then measured and an electric resistance pulse is applied to the liquid metal to measure deformed behavior of the inclusions. The resistance pulse method can be used with liquid droplets, steel slag, bubbles and other deformable inclusions.

17 Claims, 16 Drawing Sheets

250

METHOD FOR DISTINGUISHING, CLASSIFYING AND MEASURING SOFT AND HARD INCLUSIONS IN LIQUID METAL

TECHNICAL FIELD & BACKGROUND

The inclusions as particles of separate phases suspended in a liquid metal can be classified into two types, hard inclusions and soft inclusions. Hard inclusions are oxides or other non-deformable particles, such as aluminum oxide, magnesium oxide, silicon oxide, aluminum carbide, silicon carbide, titanium diboride and vanadium diboride. Soft inclusions are attributable to gas bubbles, molten slag, molten salt droplets, and agglomerates of other very small particles or other deformable inclusions. Examples of soft inclusions include chloride types which come from degassing processes using chlorine or chloride or fluxing molten metal. Soft inclusions also come from using granular salts in a furnace. Inclusions cause pinholes in foil and container sheets such as food, can sheets or beverage can sheets and are also involved with breakage of wire during drawing operations and surface defects such as streaking in automobile trim. Inclusions also serve as nucleating sites during solidification and thereby affect the stress and fatigue life of certain products.

Comparing relative harm to the quantity of a liquid metal, the gas bubbles might be less harmful than that of the hard inclusion since they generate less stress and do not nucleate as easily. Moreover, the gas bubbles can be eliminated in process treatment. The gas bubbles might form the pseudo signal similar to that of a hard particle, causing the measurement results to overestimate the inclusion concentration in the liquid metal and consequently influence the measurement accuracy of a resistive pulse technique. Therefore, it is necessary to discriminate gas bubbles from hard inclusions for high gas containing or gas sensing liquid metal or alloy when using a resistive pulse technique.

Currently, the inclusions in metal that are analyzed and classified are attributable to destructive testing and non-destructive testing. The destructive testing involves the following methods. Using a microscope, solid metal samples can help to determine qualitatively and semi-quantitatively whether an inclusion is a hard inclusion or a soft inclusion. Metallographical analysis is used to analyze the inclusions in a metal that are concentrated in a sample by passing the molten metal through a filter to search for the inclusions at the leading edge of the filter. Porous disc filtration analysis (PoDFA™) and liquid aluminum inclusion sampler (LAIS™) are two commercially available sampling systems based on metallographic analysis. Metallographic analysis provides semi-quantitative analysis, identifies the inclusion types and distinguishes between hard inclusions and soft inclusions, but does not give results in real time. Ultrasonic non-destructive testing is another method that performs an analysis only on metal in a solid state, however, it cannot identify whether an inclusion originated as a hard inclusion or a soft inclusion.

A current instrument used for measuring inclusion concentrations employs a Coulter counter as a liquid stream that passes through a flow through cell. A Coulter counter is a testing technique used for counting pulses in a liquid stream that passes through a flow through cell. The measurement principle involves measuring a voltage pulse when the inclusions pass though an electric sensing-zone by inserting a pair of electrodes inside and outside of a small flow through cell. As inclusion particles flow through this flow through cell and as the voltage between the electrodes increase, the electric sensor produces voltage pulses. The voltage pulses have amplitudes which are a function of the effective particle diameter.

Means are needed to discriminate and classify or identify the two different types of inclusions in a liquid metal stream in real time to determine the original size of soft inclusions and to identify the soft inclusion types according to their deformable behaviors. These factors influence the signal from surface tension forces that drive a free particle toward a spherical shape, whereas initial conditions and/or fluid-dynamic forces are the primary sources of forming a non-spherical shape. The method for distinguishing, classifying and measuring soft and hard inclusions in liquid metal show that the fluid-dynamic forces come from the pressure gradient due to variation of the shaped-wall and the self-induced Lorentz forces. The variation of deformation and volume shrinkage affect the drag of any bubbles and the transit time of the bubbles. passing through the flow through cell will consequently change which will be reflected on the voltage pulse measurement.

It is an object of the present invention to provide a method to discriminate and identify different types of inclusions in a liquid metal stream in real time.

It is an object of the present invention to provide a method that produces sizing information for both hard and soft inclusions according to a prototype voltage signal.

It is another object of the present invention to provide a method to identify the degree of softness for soft inclusions to discriminate gas bubbles and slag according to their deformable behaviors.

What is really needed is a method for distinguishing, classifying and measuring soft and hard inclusions in liquid metal that discriminates and identifies different types of inclusions in a liquid metal stream in real time, that provides sizing information for both hard and soft inclusions according to a prototype voltage signal and identifies the degree of softness for soft inclusions to discriminate gas bubbles and slag according to their deformable behaviors.

These and other objects of the present invention will become apparent from reference to the figures of the drawings and the detailed description which follow.

BRIEF DESCRIPTION OF THE DRAWINGS

The present invention will be described by way of exemplary embodiments, but not limitations, illustrated in the accompanying drawings in which like references denote similar elements, and in which.

DETAILED DESCRIPTION OF ILLUSTRATIVE EMBODIMENTS

Various aspects of the illustrative embodiments will be described using terms commonly employed by those skilled in the art to convey the substance of their work to others skilled in the art. However, it will be apparent to those skilled in the art that the present invention may be practiced with only some of the described aspects. For purposes of explanation, specific numbers, materials and configurations are set forth in order to provide a thorough understanding of the illustrative embodiments. However, it will be apparent to one skilled in the art that the present invention may be practiced without the specific details. In other instances, well-known features are omitted or simplified in order not to obscure the illustrative embodiments.

Various operations will be described as multiple discrete operations, in turn, in a manner that is most helpful in understanding the present invention. However, the order of description should not be construed as to imply that these operations are necessarily order dependent. In particular, these operations need not be performed in the order of presentation.

The phrase "in one embodiment" is used repeatedly. The phrase generally does not refer to the same embodiment, however, it may. The terms "comprising", "having" and "including" are synonymous, unless the context dictates otherwise.

Figure 1:
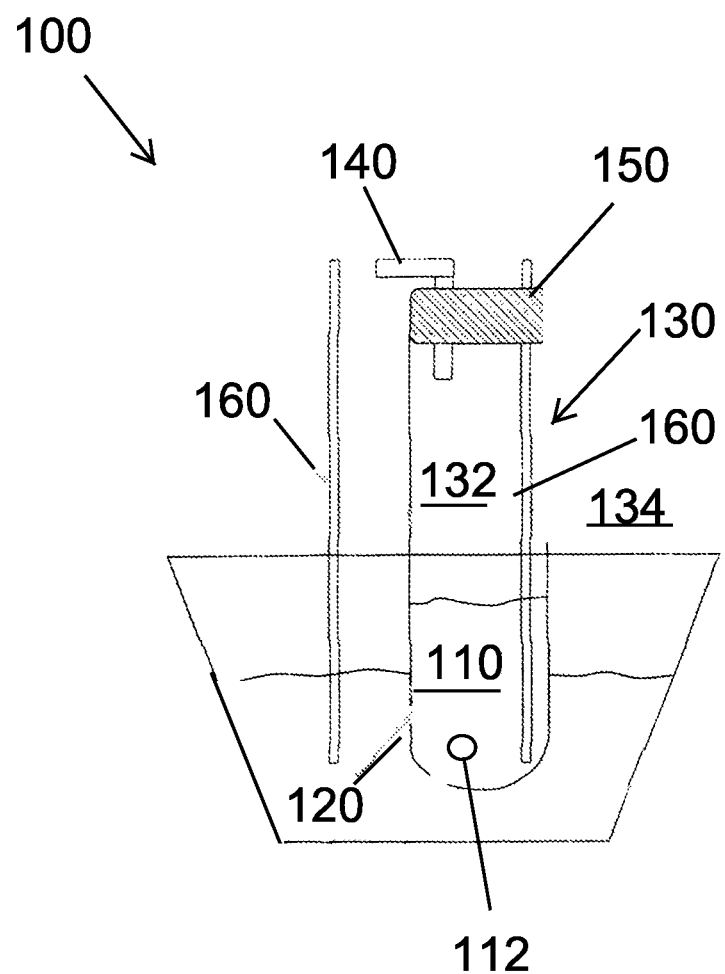
FIG. 1 illustrates a side perspective view of an apparatus utilized in a method for distinguishing, classifying and measuring soft and hard inclusions in liquid metal, in accordance with one embodiment of the present invention.

FIG. 1 illustrates a side perspective view of an apparatus utilized in a method for distinguishing, classifying and measuring soft and hard inclusions in liquid metal 100 used in an inclusions measurement of a sampled liquid metal 110, in accordance with one embodiment of the present invention. The apparatus utilized in a method for distinguishing, classifying and measuring soft and hard inclusions in liquid metal 100 is a Coulter counter. A flow through cell 120 is disposed on a tube 130 with the diameter of the flow through cell 120 being typically less than one millimeter. The tube 130 is made of quartz, but can be made of any suitable material. A vacuum system 140 is mounted on the top sealed-end 150 of the tube 130 in order to suck the sampled liquid metal 110 with suspended particles 112 into the tube 130. One or more pairs of electrodes 160 are set inside 132 and outside 134 of the tube 130 and then impose direct current in order to form a current path within the flow through cell 120, when the suspended particles 112 pass through. When the electric resistance changes from the current path, an electric resistance pulse is obtained. The number and size of the suspended particles 112 are obtained by interpreting the electric resistance pulse information that includes the peak, the width and the gradient of the electric resistance pulse.

Soft inclusions can be either gas bubbles or slag droplets that can be deformed under certain dynamic conditions in molten metal. The apparatus utilized in a method for distinguishing, classifying and measuring soft and hard inclusions in liquid metal 100 distinguishes soft inclusions through their deformed behaviours under certain fluid dynamic conditions. These deformed behaviours can be interpreted by the change of electric resistance, namely by the Coulter counter method. The deformable behaviours of soft inclusions can be described by a two-phase flow model. A numerical approach to the two-phase flow model is a level set method (LSM) that can be used in combination with the Navier-Stokes equation, which includes the self-induced electromagnetic force that results from imposing direct current on a cylindrical-like flow through cell such as the flow through cell 120.

The surface tension of coefficient between the soft inclusion and the liquid metal is relative large and the soft inclusion and the liquid metal yields a large density difference and is critical as to whether the soft inclusions can be deformable in the molten metal. The surface tension of coefficient results from the competition of surface tension forces between inertial forces and electromagnetic forces. The ability of deformation can be characterized by the Weber number for multiphase flow, which represents the ratio of liquid metal stresses, which cause deformation, to surface tension stresses, which resist deformation. It reads, $$We = (\rho_l w^2 d)/\sigma_{mi}.$$

Here, $\rho_l$ is the liquid metal density and the time-dependence relative velocity of the soft inclusion $w(t) \equiv u_{si}(t) - u_l(t)$ is defined as the relative velocities along the soft inclusion trajectory, $u_{si}(t)$, $u_l(t)$, which are the velocities of the soft inclusion and the liquid metal. d is the mean diameter of the soft inclusion and $\sigma_{mi}$ is the surface tension coefficient between the liquid metal and the soft inclusion. Note that $\sigma_{mi}$ yields a relatively large value where the surface tension coefficient of aluminium and gas bubbles is about 1 [N/m] and that of liquid steel and gas bubbles is about 1.2·1.8 [N/m], depending on the kind of steel (i.e. sulphur or oxygen concentration) used, steel and slag droplets are about 0.6 [N/m]. When the Reynolds number of a gas bubble ($Re_b = (\rho_l |w| d)/\mu_l$) is moderate, and the Weber number equal approaches or larger than unit, the soft inclusion can be deformed in the liquid metal. For example, a gas bubble that is existing in molten aluminium, when $\sigma_{mi}=1$ [N/m], d=200 [μ/m], ρ=2700 [kg/m³], w=2 [m/s], then the Weber number is We=2.16.

Figure 2A:
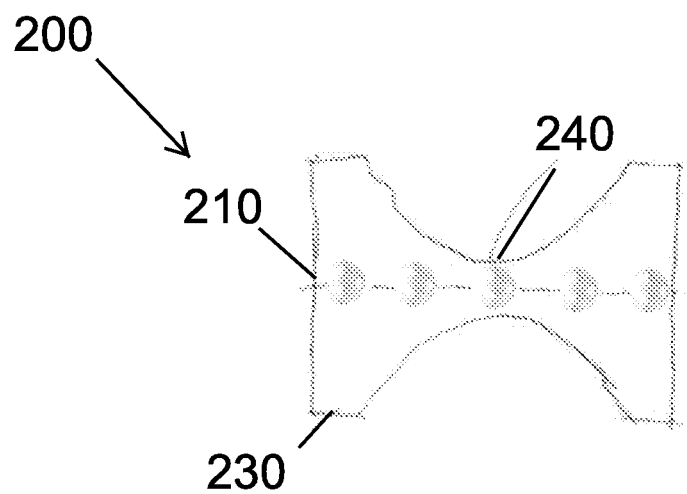
FIG. 2A illustrates a side perspective view of a hard inclusion passing through a flow through cell, in accordance with one embodiment of the present invention.
Figure 2B:
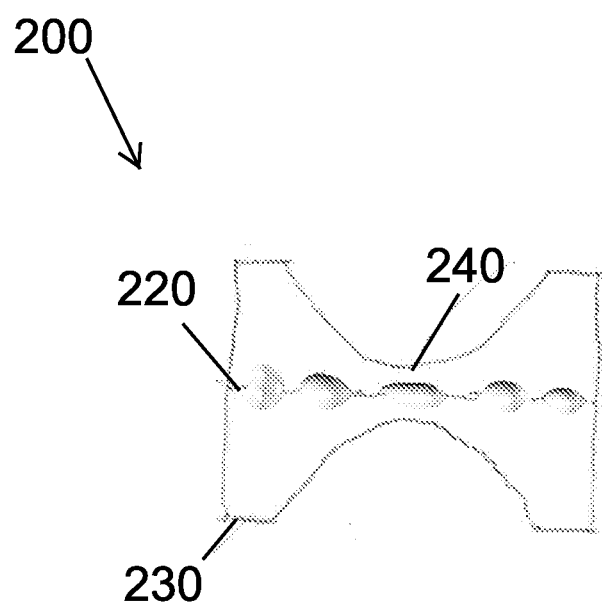
FIG. 2B illustrates a side perspective view of a soft inclusion passing through a flow through cell, in accordance with one embodiment of the present invention.
Figure 2C:
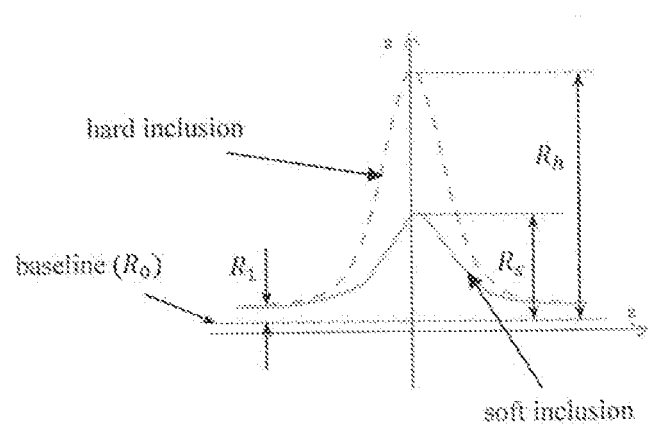
FIG. 2C illustrates a graphical comparison of electric resistance pulses of hard and soft inclusions, in accordance with one embodiment of the present invention.

FIG. 2A illustrates a side perspective view of a hard inclusion 210 passing through a flow through cell 200, in accordance with one embodiment of the present invention. FIG. 2B illustrates a side perspective view of a soft inclusion 220 passing through a flow through cell 200, in accordance with one embodiment of the present invention. FIG. 2C illustrates a graphical comparison of electric resistance pulses of hard and soft inclusions 250, in accordance with one embodiment of the present invention. As illustrated in FIG. 2A, the hard inclusion 210 is spherical shape and does not deform as it passes through the flow through cell 200 while a centrally-symmetrical resistance pulse can be obtained in term of space-dependence. In contrast, as illustrated in FIG. 2B, the soft inclusion 220 is also spherical shape and does deform as it passes through the flow through cell 200 while a centrally-symmetrical resistance pulse can be applied in term of space-dependence. The soft inclusion 220 can successively deform when it passes through the flow through cell 200 due to the resistance signal since its peak pulse is much lower than that of the hard inclusion 210 and the pulse in terms of space dependence is no more centrally-symmetrical physically as well.

When the number and size of the inclusions 210,220 are measured from a liquid metal sample normally in a couple of seconds, the electric resistance of the sampling liquid metal or alloy without suspension of inclusion as initial resistance $R_0$ within the electric sensing-zone in the flow through cell is determined. When a hard inclusion 210 or a soft inclusion 220 passes through the first stage 230 of the flow through cell 200, the inclusion 210,220 registers the resistance value, $R_1$, when the inclusion 210,220 passes through the second stage 240 of the flow through cell 200, the peak resistance values of the hard inclusions 210 and the soft inclusions 220 are $R_h$, $R_s$. The hard inclusions 210 and the soft inclusions 220 are identified by comparing the ratios of $R_h/R_1$ and $R_s/R_1$, the said ratio of the soft inclusions 220 are distinctly smaller than that of the hard inclusions 210, which are not dependent on the size of the inclusions 210,220. Hence, there exists a threshold value $R_\tau$, when $R_h/R_1 < R_\tau$, the inclusion is a soft inclusion 220, otherwise, the inclusion is a hard inclusion 210. The sizes of the hard inclusions 210 can then be determined according to the electric resistance values applied in the first stage 230 of the flow through cell 200 or the second stage 240 and the size of the soft inclusion 220 can be determined according to the electric resistance value applied in the first stage 230 of the flow through cell 200. The formula $R=4\rho_e d^3/\pi D^4$, can then be applied, where $\rho_e$ is resistivity of liquid metal, d is the diameter of inclusion and D is the throat diameter of flow through cell. The formula must be corrected by a factor $f(d/D)=[1-(d/D)^{0.8}]^{-1}$.

$R_1$ compared to the peak value $R_h$ and $R_s$ is relative smaller. To determine its value, the baseline of a signal, which involves the filter and amplification of the signal in accordance with the pulse character of the soft and hard inclusions, such as a peak value, gradient trends of starting and endings of any pulse should be determined, to determine the entire pulse signal. The transit time can also be utilized to determine how the inclusion passes through the cell 200.

The primary factors that influence soft inclusion deformation include the shape of the passage path, which is the flow through cell 200 that the sampling liquid metal with soft inclusions flow through, the velocity field within the flow through cell 200, the vacuumed flow rate of the sampling liquid metal, which can be controlled and adjusted by a vacuum system (not shown) and a self-induced electromagnetic force exerted by an applied direct current, which influences bubble deformation. A large pressure gradient deforms the soft inclusion 220 based on the design of the flow-through cell or flow-through cell 200.

Figure 3A:
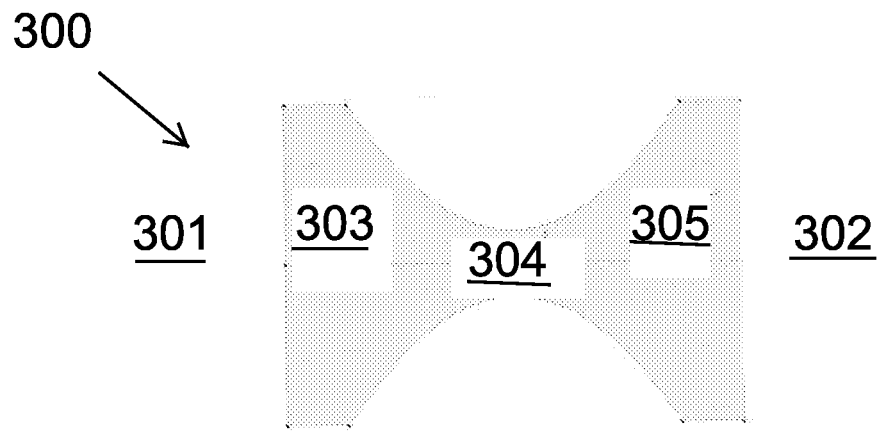
FIGS. 3A, 3B and 3C illustrate three types of fluid pass through cells or flow through cells with different shaped walls, in accordance with one embodiment of the present invention.
Figure 3B:
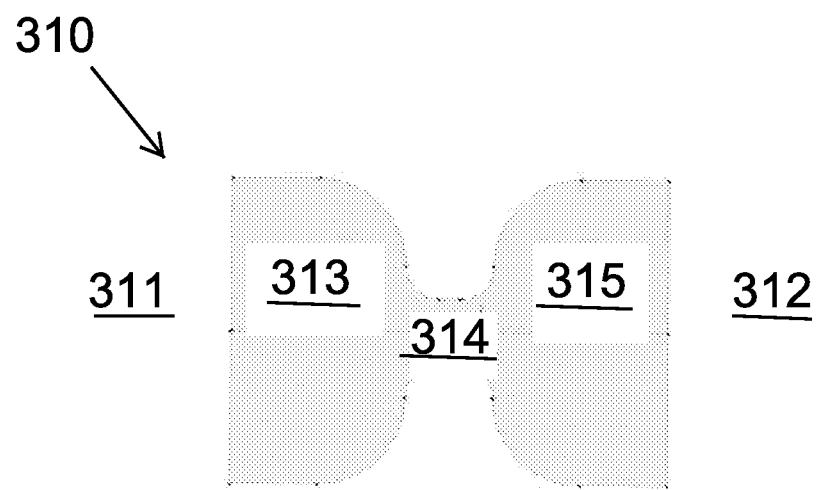
Figure 3C:
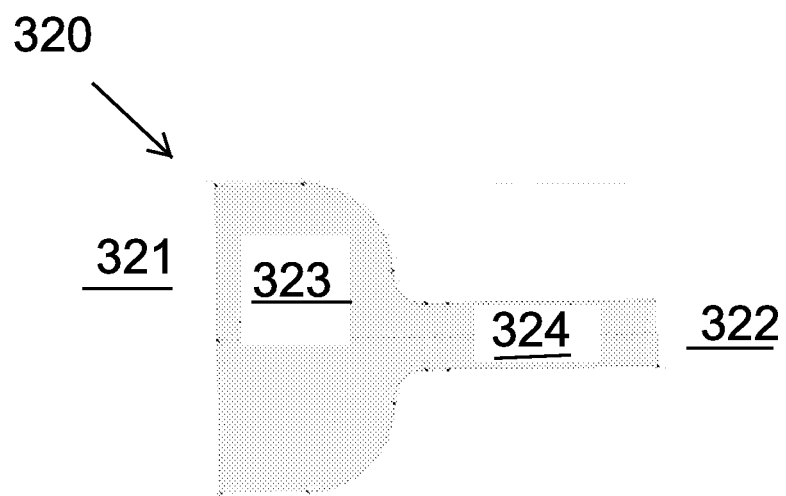

FIGS. 3A, 3B and 3C illustrate three types of fluid pass through cells or flow through cells 300,310,320 with different shaped walls, in accordance with one embodiment of the present invention. The three types of flow through cells 300,310,320 with different shaped walls help to distinguish between and measure a soft inclusion from a hard inclusion (inclusions not shown in FIGS. 3A, 3B and 3C).

The first type of flow through cell has a bowtie shape 300, which can obtain a high pressure gradient near the throat 304 of the bowtie-shaped flow through cell in order to deform any soft inclusion. In order to validate the measuring results of a sampling liquid metal (not shown in FIGS. 3A, 3B, 3C), the bowtie-shaped flow through cell 300 is designed to make it possible for the sampling liquid metal to enter the bowtie-shaped flow through cell 300 either from the left side 301 of the bowtie shaped flow through cell 300 or from the right side 302 of the bowtie shaped flow through cell 300. The bowtie-shaped flow through cell 300 has a left section 303, a narrowing middle throat 304 and a right section 305. The left section 303 and right section 305 are vertical mirror images to each other and can both receive hard inclusions or soft inclusions.

The second type of flow through cell is a second bowtie-shaped flow through cell 310, which is also designed to make it possible for the sampling liquid metal to enter the second bowtie-shaped flow through cell 310 either from the left side 311 of the second bowtie shaped flow through cell 310 or from the right side 312 of the second bowtie shaped flow through cell 310. The bowtie-shaped flow through cell 310 has a left section 313, a narrowing middle throat 314 and a right section 315. The left section 313 and right section 315 are vertical mirror images to each other and can both receive hard inclusions or soft inclusions. The narrowing middle throat 314 of the second bowtie-shaped flow through cell 310 is shorter horizontally in length than the narrowing middle throat 304 of the first bowtie-shaped flow through cell 300.

The third type of flow through cell is a funnel-shaped flow through cell 320, which is also designed to make it possible for the sampling liquid metal to enter the funnel-shaped flow through cell 320 either from the left side 321 of the funnel-shaped flow through cell 320 or from the right side 322 of the funnel-shaped flow through cell 320. The funnel-shaped flow through cell 320 has a left section 323 and a relatively narrow right section 324. The left section 323 and right section 324 can also both receive hard inclusions or soft inclusions.

All of the three types of flow through cells, the bowtie-shape flow through cell 300, the second bowtie-shaped flow through cell 310 and the funnel-shaped flow through cell 320 can be fabricated by techniques utilizing a laser and/or a rotary grinding tool.

Figure 4:
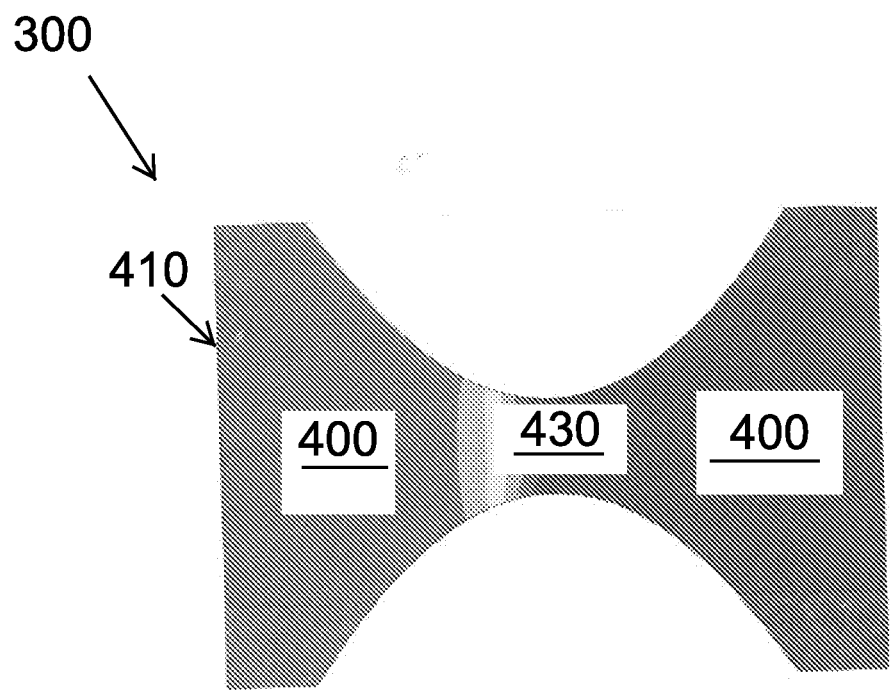
FIG. 4 illustrates a side perspective view of a pressure distribution within a flow through cell, in accordance with one embodiment of the present invention.

FIG. 4 illustrates a side perspective view of a pressure distribution 400 within a flow through cell 410, in accordance with one embodiment of the present invention. The type of flow through cell 410 illustrated in FIG. 4 is the same as the first bowtie-shaped flow through cell 300 described in FIG. 3A. The pressure gradient mainly concentrates near the narrowing middle throat 430, where the pressure drop can reach up to $10^3$ [Pa] within this small region in the horizontal direction with an initial velocity of 0.1 [m/s].

Figure 5:
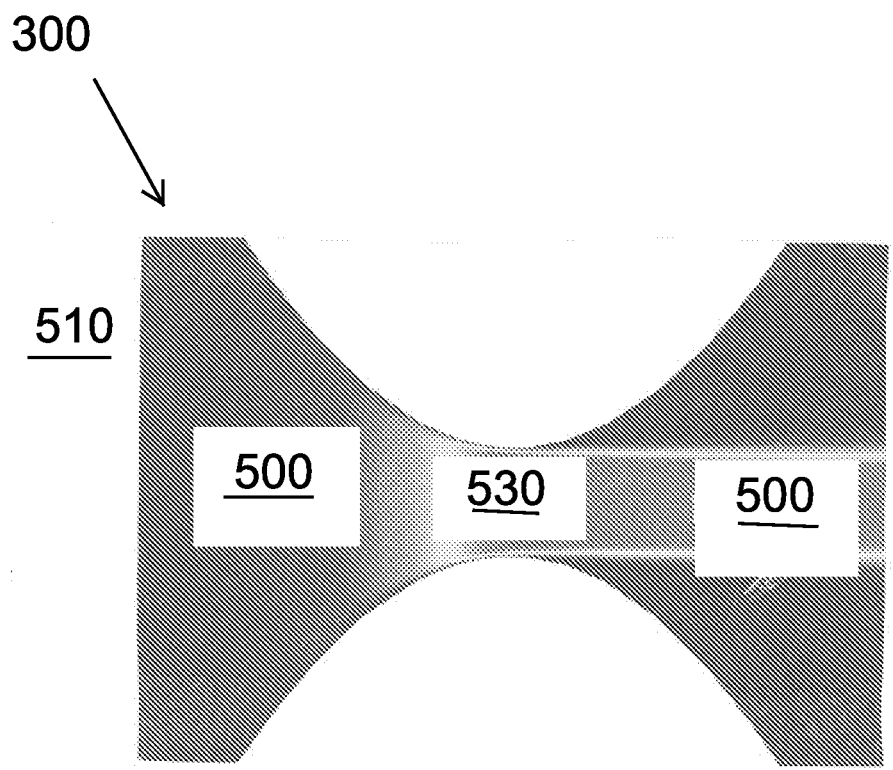
FIG. 5 illustrates a side perspective view of a velocity field within a flow through cell, in accordance with one embodiment of the present invention.

FIG. 5 illustrates a side perspective view of a velocity field 500 within a flow through cell 510, in accordance with one embodiment of the present invention. The type of flow through cell 510 illustrated in FIG. 5 is the same as the first bowtie-shaped flow through cell 300 described in FIG. 3A. The velocity field 500 is a typically rapid, smoothly converging and micro-fluidic within a shape-varying short duct. When the ratio of entrance and the flow through cell 510 is large, even with a small initial velocity, it forms a significant jet flow. Assuming that the inlet velocity is 0.1 [m/s], which can be interpreted as an equivalent pressure setting by a vacuum system (not shown in FIG. 5), the velocity increases sharply near the narrowing middle throat 520 of the flow through cell 510 up to about several meters per second depending on the angle of the wall of the flow through cell 510 and then maintains a high velocity further down the flow through cell 510. Although the velocity of any inclusions are high and the typical length of the flow through cell 510 is small, the Reynolds number is about 2000 and the flow itself is still in the laminar regime.

Figure 6:
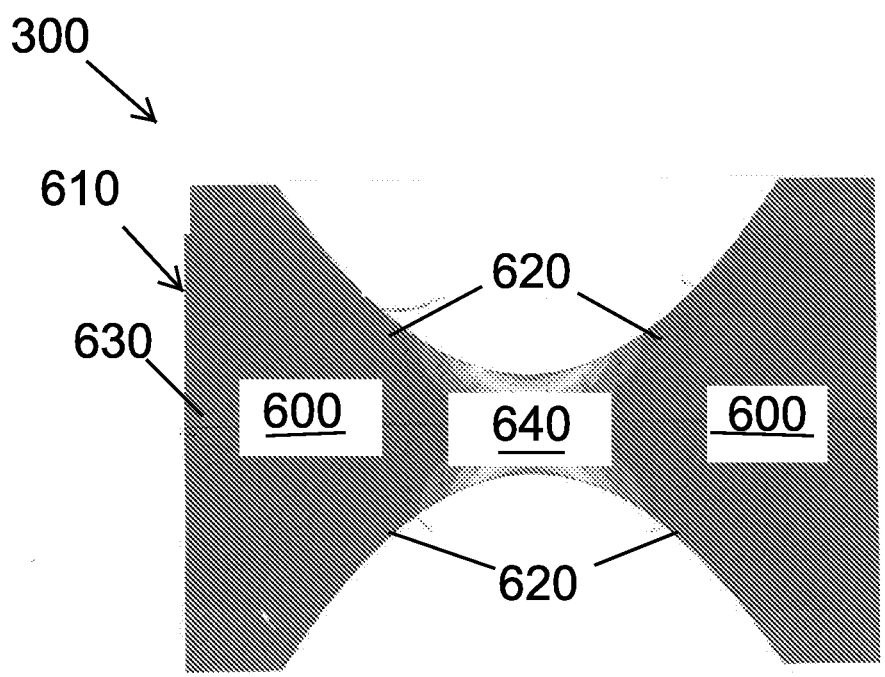
FIG. 6 illustrates a side perspective view of a self-induced electromagnetic force distribution within a flow through cell, in accordance with one embodiment of the present invention.

FIG. 6 illustrates a side perspective view of a self-induced electromagnetic force distribution 600 within a flow through cell 610, in accordance with one embodiment of the present invention. The force density can be represented with colors, without a particle passing through a cell 610, utilizing the electromagnetic force distribution in the throat 640 of the cell 610 according to basic electromagnetism theory, where the maximum force values appear close to the wall 620 of the throat 640 and gradually decrease toward the vertical axis (no number) of the cell 610. When an inclusion passes through the cell 610, because it is a non-conducting substance and does not yield an electromagnetic force and the electromagnetic force density becomes squeezed. It results in bubble deformation and a transit time change with the change of the electromagnetic force, where the transit time change will reflect on the resistive pulse and change the shape of resistive pulse.

FIGS. 7A, 7B, 7C and 7D illustrate side perspective views of a gas bubble 710 passing through different locations within a flow through cell 700, in accordance with one embodiment of the present invention. The gas bubble 710 is a spherical shaped air bubble, the high surface tension coefficient between the bubble 710 and the liquid metal, make the bubble 710 appear as a perfect sphere. The gas bubble 710 passes through a molten aluminium medium 720 through the flow through cell 700 and illustrates the competition of the surface tension force and the inertial effect and self-induced electromagnetic force on the gas bubble 710. When the gas bubble 710 moves closer to the narrowing middle throat 730 of the flow through cell 700, the competition of the surface tension force and the inertial effect and self-induced electromagnetic force results in a successive deformation of the gas bubble 710, assuring that the gas bubble 710 can successfully pass through the flow through cell 700. Because of the large difference of the electric conductivity between the gas bubble 710 and the liquid aluminium medium 720, such deforming must affect the pulse of the electric resistance of the gas bubble 710 and the aluminium medium 720. Comparing the pulse of a hard inclusion (not shown in FIGS. 7A-D) with a same sized gas bubble 710, the pulse of a gas bubble 700 becomes wider and the peak value of the gas bubble 710 becomes smaller. The transit time of a soft inclusion passing through the flow through cell 700 is in milliseconds.

Figure 7A:
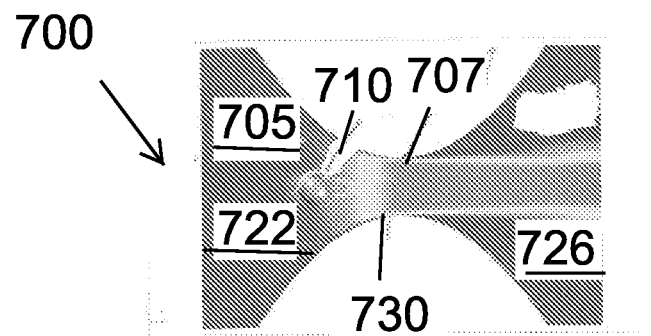
FIGS. 7A, 7B, 7C and 7D illustrate side perspective views of a gas bubble passing through a flow through cell, in accordance with one embodiment of the present invention.

FIG. 7A illustrates a gas bubble 710 moving through a flow through cell 700 as a vacuum (not shown in FIGS. 7A-D) is applied to the gas bubble 710 as the gas bubble 710 is drawn through the flow through cell 700. The liquid aluminum medium 720 can also be drawn from inside of the flow through cell 700 to the outside of the flow through cell 700 using a vacuum. This can be used to confirm the pulses measured and be expressed as a distribution of electromagnetic force density and direction. After classifying hard and soft inclusions, the size of the hard and soft inclusions can also be determined by the resistance formed in the first part 705 of the flow through cell 700.

Figure 8A:
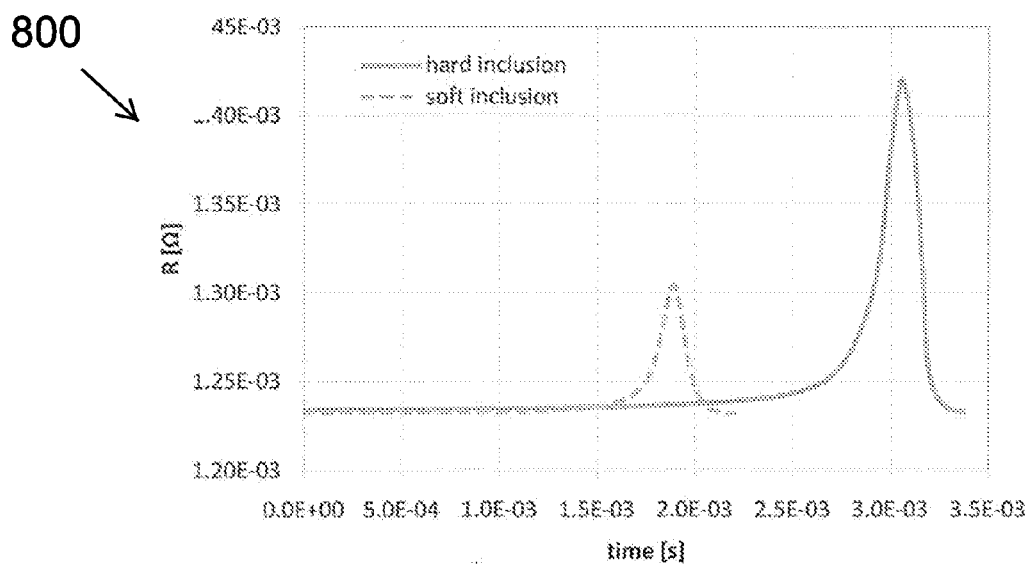
FIGS. 8A and 8B illustrate graphical comparisons of space-dependence and time-dependence pulses of hard and soft inclusions, in accordance with one embodiment of the present invention.
Figure 8B:
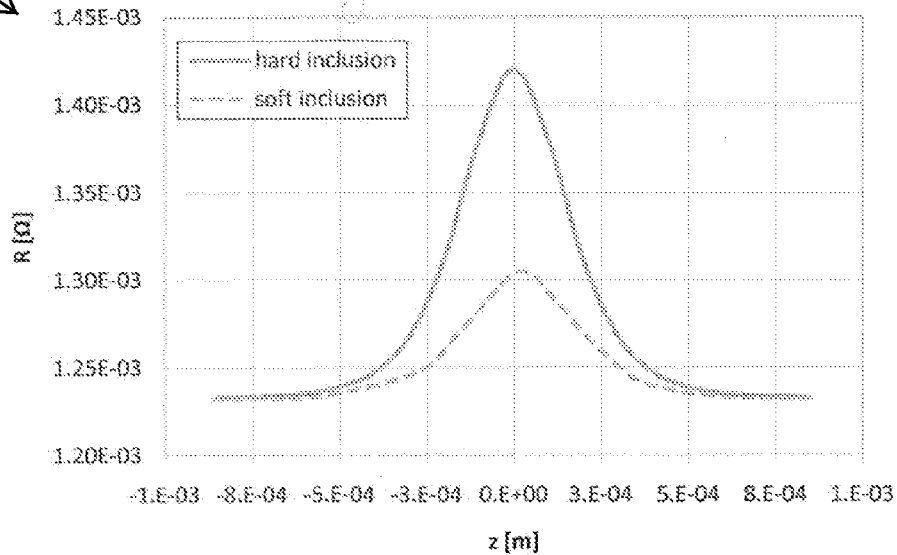

FIGS. 8A and 8B illustrate graphical comparisons of space-dependence and time-dependence pulses of hard and soft inclusions 800, 810, in accordance with one embodiment of the present invention. The signals from space-dependence into time-dependence can be computed by the gas bubble trajectories. The discussion of space-dependence pulses involving hard and soft inclusions was previously described in the FIGS. 2A and 2B descriptions.

Figure 9:
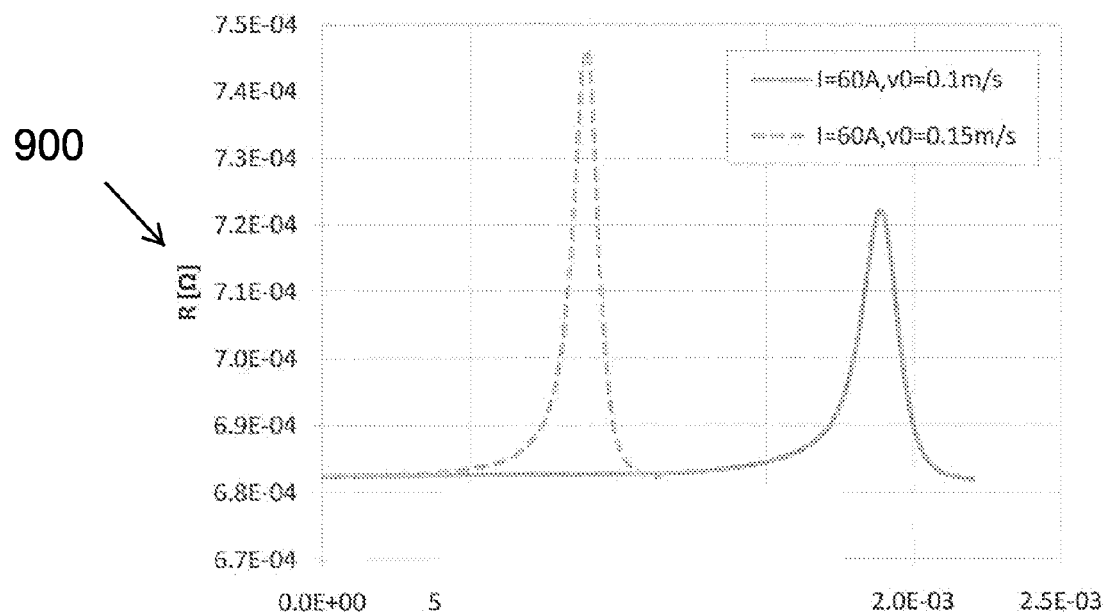
FIG. 9 illustrates a graph showing the influence of velocity on the deformation of a soft inclusion, in accordance with one embodiment of the present invention.

Classifying and distinguishing soft inclusions and hard inclusions is based on the inertial force of the liquid metal sample that can deform the soft inclusions and leave the hard inclusions unaffected. Different inertial forces induce soft inclusions being deformed to different degrees and therefore obtain different pulses. FIG. 9 illustrates a graph showing the influence of velocity on the deformation of a soft inclusion 900, in accordance with one embodiment of the present invention. Specifically, FIG. 9 illustrates the influence of the initial velocities of 0.1 [m/s] and 0.15 [m/s] on the pulse of a soft inclusion, with the peak difference of the pulses reaching up to approximately 30%. Different inward and outward vacuum pressures can be applied to the soft inclusion thereby obtaining different flow rates or initial velocities. The pulses of hard inclusions keep the same peak-values but different transit times during inward and outward vacuum processes with different velocities. By setting velocity differences or imposing different DC current inward and outward of the tube, we can classify and measure soft inclusions. In contrast, soft inclusions yield different peak-values of resistance pulses and can be classified and distinguished differently than hard inclusions. Furthermore, with the resistance of $R_1$ mentioned previously, the original sizes of soft inclusions can be easily determined.

Soft inclusions can also be classified and distinguished from hard inclusions by setting different direct currents between two electrodes, as illustrated in FIG. 1, where inward and outward vacuum pressures can be performed on the same liquid metal sample. The flow rates are kept constant and the amount of direct current is varied. For soft inclusions, the larger the direct current, the larger the electromagnetic force is and the larger the deformation of the bubble is, while physically reducing the peak-values of the pulse. In contrast, the peak-values of pulses of hard inclusions are not affected by an input direct current.

Figure 10:
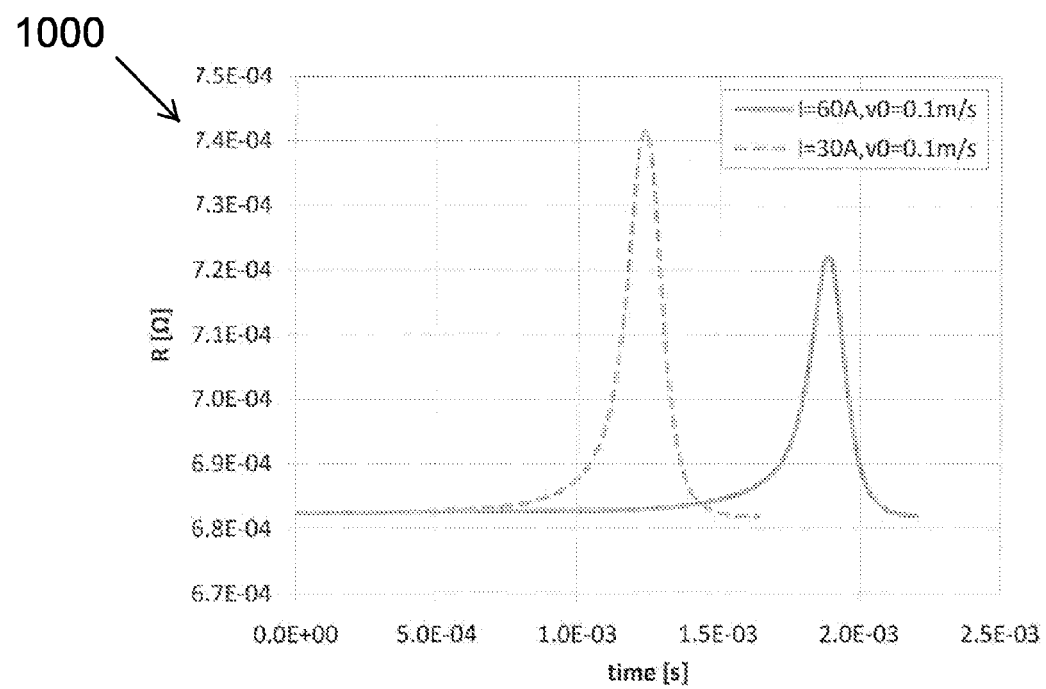
FIG. 10 illustrates a graph showing the influence of a self-induced electromagnetic force on the deformation of a soft inclusion, in accordance with one embodiment of the present invention.

FIG. 10 illustrates a graph showing the influence of a self-induced electromagnetic force on the deformation of a soft inclusion 1000, in accordance with one embodiment of the present invention. Specifically, FIG. 10 shows the pulses of soft inclusions under direct currents of 30 Amps and 60 Amps.

EXAMPLE 1

Classify and Measure Gas Bubble from Hard Inclusion in Liquid Aluminum

The two-phase flow includes gas bubbles and an immiscible liquid metal with a flow regime that is laminar and incompressible and the moving boundaries in which the geometry's topology changes with time is simulated by the level set method. The level set method is a promising numerical approach to track the boundary for the two-phase flow. The Eulerian-Lagrange Approach (ELA) is used to simulate the two-phase flow behaviors of a hard inclusion suspension. The liquid metal flow is modeled with the Eulerian approach while the particle motion is computed with the Lagrange approach.

Figure 7B:
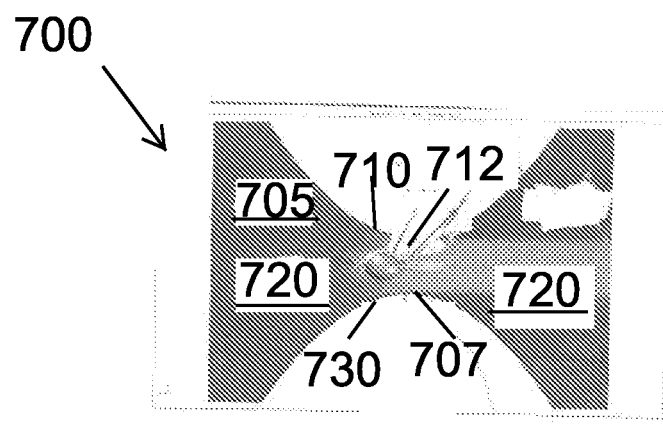
Figure 7C:
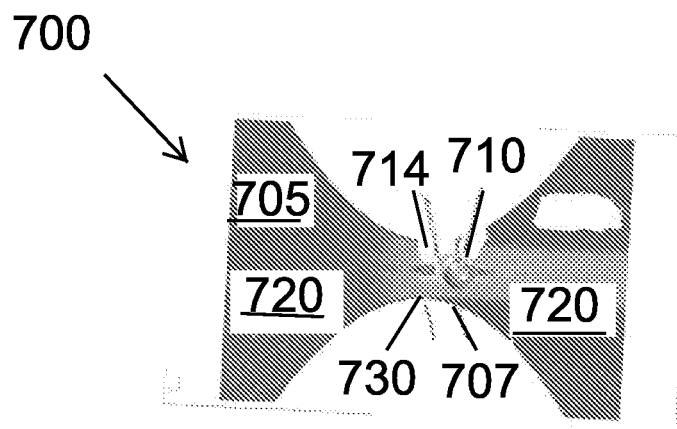
Figure 7D:
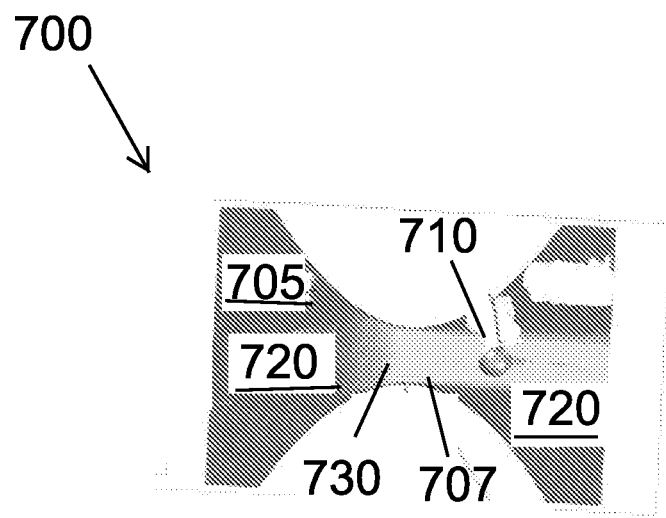

As illustrated in FIGS. 7A, 7B, 7C and 7D, an air bubble 710 successively deforms when it flows through a flow through cell 700. Here we shows four moments (t=0.1 ms, t=0.12 ms, t=0.13 ms, and t=0.14 ms) and the flow field of liquid aluminium is shown as well. The air bubble 710 almost does not deform when it passes through the first part 705 of the flow through cell 700, but in the second part 707 of the flow through cell 710, i.e. at t=0.1 ms, seen in FIG. 7A, the air bubble 710 starts to be compressed due to the shrinkage flow and magnetic pressure increase. The air bubble 710 becomes elongate at the throat 730 of the flow through cell 700 as seen in FIG. 7B and in this short period, an irregular velocity region forms in front of the tip 712 of the air bubble 710, since the deformation retards the bubble movement. When the air bubble 710 leaves the throat 730 as seen in FIG. 7C, the high surface tension makes the air bubble 710 and a tail 714 is formed at the end of the air bubble 710. As the fluid acceleration become more effective, the tail 714 disappears and makes the air bubble 710 deform in the opposite direction and the air bubble 710 concaves.

Figure 11A:
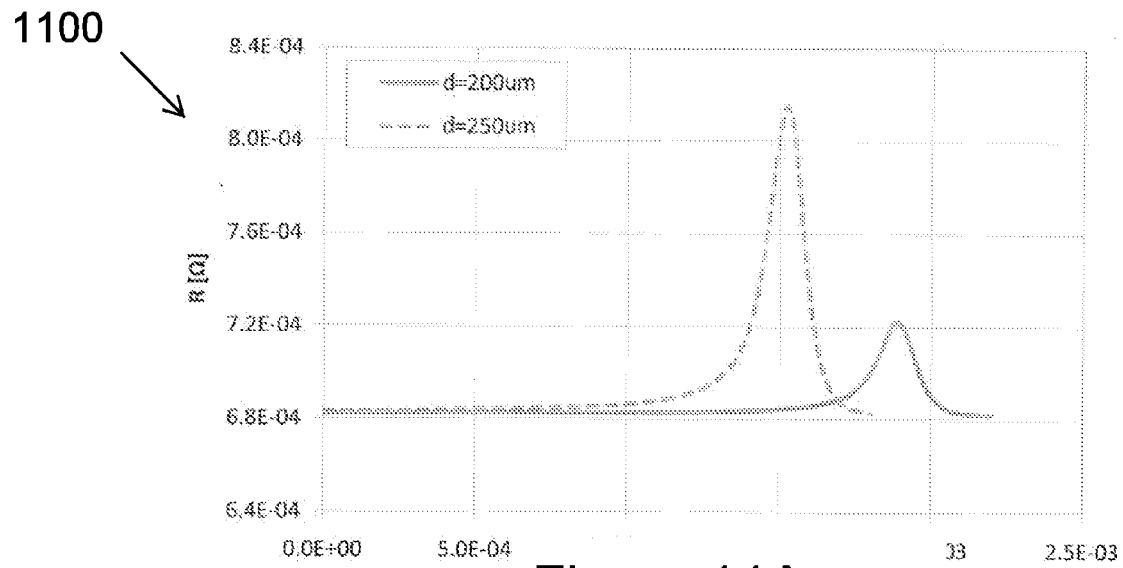
FIGS. 11A and 11B illustrate two graphs of different sized soft inclusions producing different electric resistance pulses, in accordance with one embodiment of the present invention.
Figure 11B:
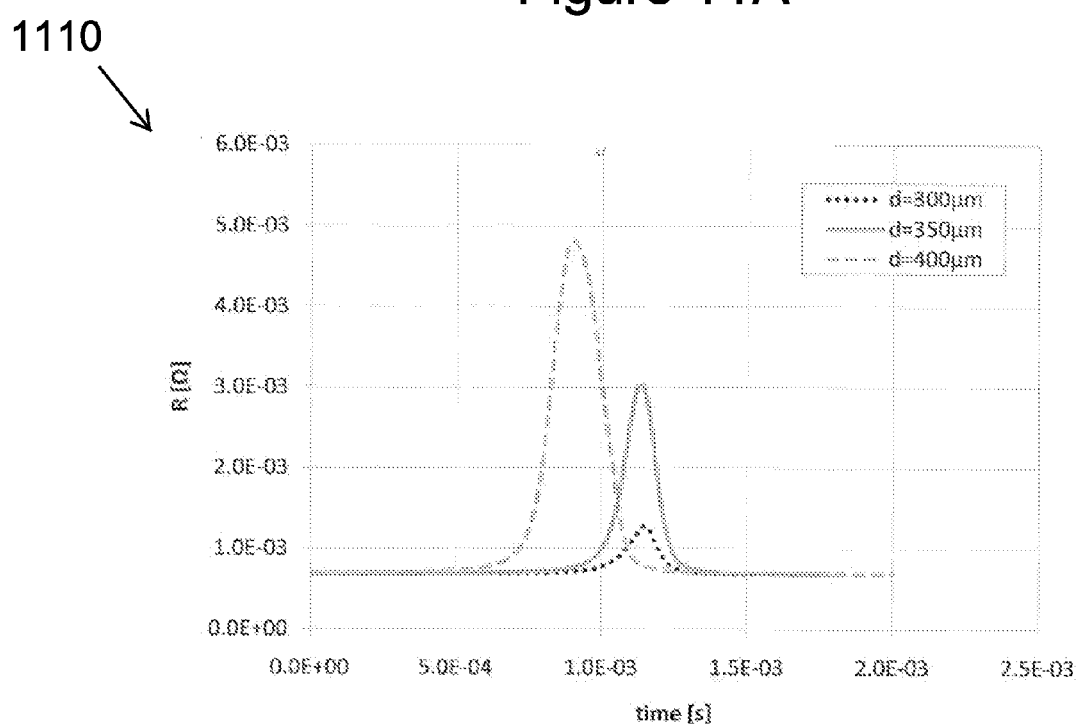

FIGS. 11A and 11B illustrate two graphs of different sized soft inclusions producing different electric resistance pulses 1100, 1110 in accordance with one embodiment of the present invention. As the size of the gas bubble increases, the peak of resistive pulse increases as indicated in FIG. 11A. Due to the deformation of the bubble, the size of the bubble is equal to or is even larger than the throat diameter that it can pass through, as illustrated in FIG. 11B.

EXAMPLE 2

To classify and measure gas bubbles and/or slag from a hard inclusion in molten steel, we detect a gas bubble or steel slag suspended in the molten steel, due to the electric conductivity of liquid steel ($0.72 \times 10^6$ [S/m]) being lower than that of liquid aluminum ($2.5 \times 10^6$ [S/m]) and to get proper pulses, we only need input of 20 Amps of direct current. The surface tension coefficient of steel and bubble $\sigma_{steel-air}$ is larger than that of aluminum and gas bubble $\sigma_{Al-air}$, where $\sigma_{steel-air} \sim 1.2$-$1.8$ [N/m]. When an air bubble flows through the flow through cell in FIG. 3A and utilizes a molten steel medium, the bubble can be deformed as well.

Figure 12:
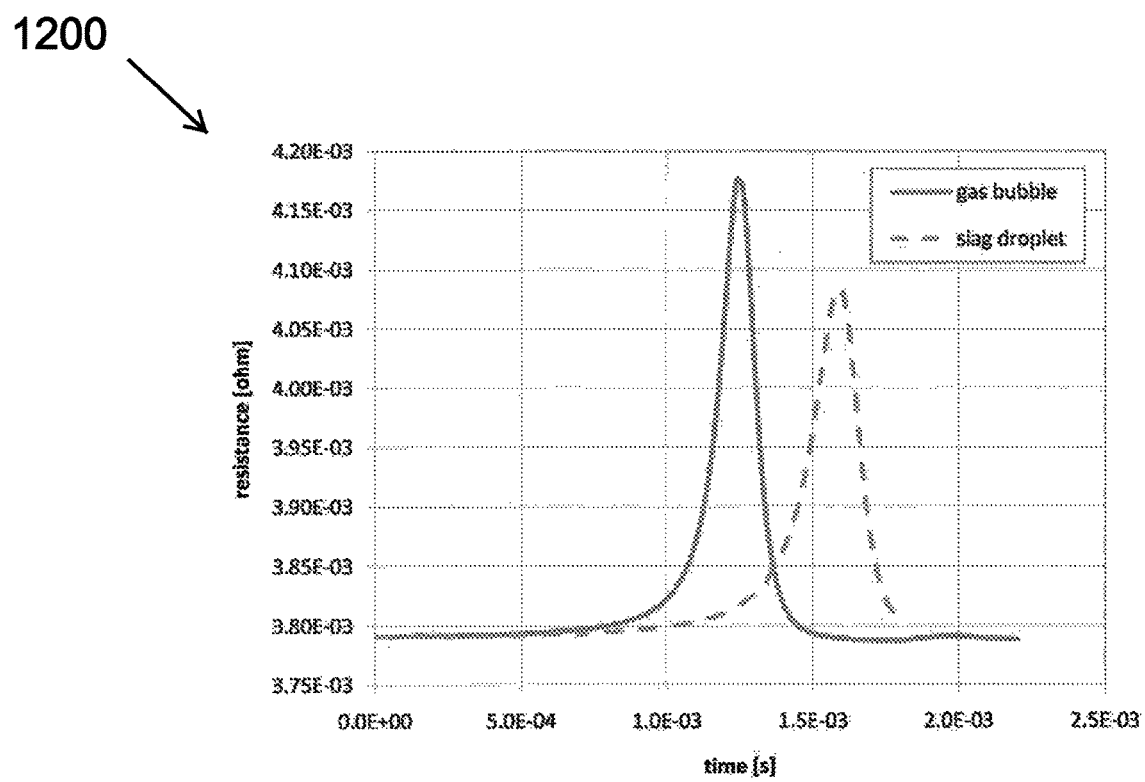
FIG. 12 illustrate a graph of a pulse characteristic of a droplet of slag in liquid steel passing through a flow through cell, in accordance with one embodiment of the present invention.

FIG. 12 illustrates a graph of a pulse characteristic of a droplet of slag in liquid steel passing through a flow through cell 1200, in accordance with one embodiment of the present invention. The resistive pulse of gas bubbles can be used to classify and measure the gas bubbles and slag droplet from hard inclusions in the molten steel. Steel slag is an important defect element in molten metal in different processes of steel production and can be an impurity in the liquid metal. It is important to avoid entrapping too much slag into any liquid steel, especially if the slag is large sized.

The surface tension coefficient of steel and slag is about 0.6 [N/m], its density is lower than that of liquid steel. Therefore, the slag is more easily deformable than the gas bubble and can be identified with the resistive pulse generated by the slag from that of the gas bubbles or hard inclusions based on the fact of its low surface tension coefficient, where the threshold value $R_\tau$ is different, $R_{\tau_{slag}} < R_{\tau_{bubble}}$ by comparing the values $R_{slag}/R_1$, $R_s/R_1$ and $R_h/R_1$. Similarly, we can determine the pulse formed by steel slag. FIG. 12 shows the resistance pulses of a soft inclusion and a droplet of slag under the same conditions, where the peak-values of the slag is lower than that of the gas bubble. In conclusion, the variation of the inclusions' trajectories have relatively little influence on the pulse, which is what would be expected.

Figure 13:
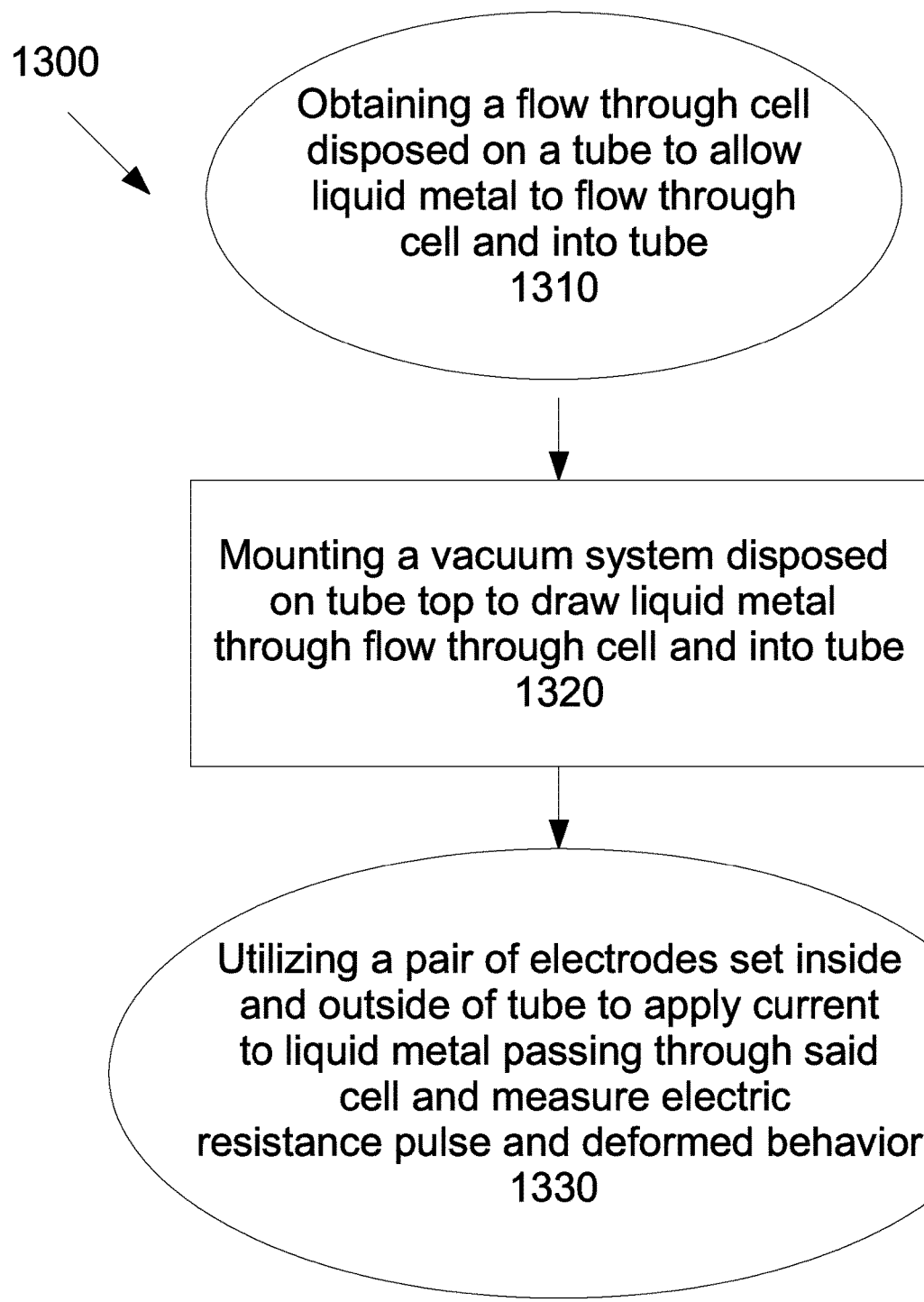
FIG. 13 illustrates a flowchart of a method for distinguishing, classifying and measuring soft and hard inclusions in liquid metal, in accordance with one embodiment of the present invention.

FIG. 13 illustrates a flowchart of a method for distinguishing, classifying and measuring soft and hard inclusions in liquid metal 1300, in accordance with one embodiment of the present invention. The steps of the overall method 1300 include obtaining a flow through cell disposed on a tube with a top to allow the liquid metal to flow through the flow through cell and into the tube 1310, mounting a vacuum system disposed on top of the tube to draw the liquid metal through the flow through cell and into the tube 1320 and utilizing a pair of electrodes set inside and outside of the tube to apply an electric current to the liquid metal passing through the flow through cell and an electric resistance change is measured and an electric resistance pulse is applied to the liquid metal to measure deformed behavior of the inclusions 1330.

While the present invention has been related in terms of the foregoing embodiments, those skilled in the art will recognize that the invention is not limited to the embodiments described. The present invention can be practiced with modification and alteration within the spirit and scope of the appended claims. Thus, the description is to be regarded as illustrative instead of restrictive on the present invention.

What is claimed is:

1. A method for distinguishing, classifying and measuring a plurality of soft inclusions and a plurality of hard inclusions in a liquid metal, comprising:
   obtaining a flow through cell with an orifice disposed on a tube with a top to allow said liquid metal to flow through said flow through cell and into said tube, wherein a plurality of shape walls of said orifice of said flow through cell are used to classify and measure said soft inclusions;
   mounting a vacuum system disposed on said top of tube to draw said liquid metal through said flow through cell and into said tube;
   utilizing a pair of electrodes with a positive electrode set inside of said tube and a negative electrode outside of said tube to apply an electric current to said liquid metal passing through said flow through cell and to measure an electric resistance change;
   applying an electric resistance pulse to said liquid metal to measure behavior of said inclusions, when said hard inclusions or said soft inclusions pass through a first stage of said flow through cell, said hard inclusions or said soft inclusions register a resistance value, $R_1$, when said hard inclusions or said soft inclusions pass through a second stage of said flow through cell, a plurality of peak resistance values of said hard inclusions is $R_h$, and a plurality of peak resistance values of said soft inclusions is $R_s$;
   identifying said hard inclusions and said soft inclusions by comparing a pair of ratios of $R_h/R_1$ and $R_s/R_1$, said ratio of said soft inclusions are smaller than said ratio of hard inclusions, wherein there exists a threshold value R and when $R_h/R_1$ is less than R, said inclusions are said soft inclusions, otherwise, said inclusions are said hard inclusions;

determining a plurality of hard inclusions sizes according to said electric resistance pulse applied in said first stage of said flow through cell or said second stage of said flow through cell;

determining a plurality of soft inclusions sizes according to said electric resistance pulse applied in said first stage of said flow through cell;

classifying and measuring said inclusions by setting a velocity field inward and outward of said tube with said sampling liquid metal and imposing different DC current inward and outward of said tube with said sampling liquid metal.

2. The method according to claim 1, wherein said tube is made of quartz or other non-conducting, high thermal stability material.

3. The method according to claim 1, wherein said flow, through cell has a bowtie-shape with a short middle throat, a bowtie-shape with a long middle throat or a funnel-shape.

4. The method according to claim 3, wherein said bowtie-shape flow through cells are vertical mirror images and said behavior is influenced by said shapes of flow through cell.

5. The method according to claim 1, wherein said soft inclusions are measured by a combination of said electric resistance pulse and a plurality of other electromagnetic methods.

6. The method according to claim 1, wherein said velocity field is applied to said flow through cell, which is interpreted as an equivalent pressure setting by said vacuum system.

7. The method according to claim 1, wherein said flow-through cell yields a pressure gradient.

8. The method according to claim 1, wherein a number, a size and said behavior of said inclusions are obtained by said electric resistance pulse information.

9. The method according to claim 8, wherein said electric resistance pulse information includes a peak measurement, a width measurement and gradient of said electric resistance pulse.

10. The method according to claim 9, wherein said behavior of soft inclusions are described in a two-phase flow model.

11. The method according to claim 10, wherein said two-phase flow model is numerically expressed using a level set method or LSM.

12. The method according to claim 1, wherein said behavior is characterized using a Weber number for multi-phase flow.

13. The method according to claim 1, wherein said hard inclusions do not deform while passing through said flow through cell when said electric resistance pulse is obtained.

14. The method according to claim 1, wherein a Coulter counter apparatus is utilized with a plurality of other electromagnetic methods to interpret said electromagnetic pulse.

15. The method according to claim 1, wherein said soft inclusions are a plurality of gas bubbles, a plurality of slag droplets, steel slag or a plurality of other deformable oxides that suspend in said liquid metal.

16. The method according to claim 1, wherein said liquid metal is aluminum, tin, magnesium, copper, steel or aluminum, tin, magnesium, copper or their alloys which yield high electric conductivities.

17. The method according to claim 1, wherein said soft inclusions are measured and classified by setting a velocity difference or imposing a plurality of different DC currents inward and outward of said tube.

\* \* \* \* \*